United States Patent [19]

Gainer et al.

[11] Patent Number: 4,973,727

[45] Date of Patent: Nov. 27, 1990

[54] METHOD FOR PREPARATION OF METAL SALTS OF METHYL PHOSPHONIC ACIDS

[75] Inventors: James Gainer, Boothstown; Donald R. Randell, Stockport, both of England

[73] Assignee: Ciba-Geigy Corporation, Ardsley, N.Y.

[21] Appl. No.: 300,463

[22] Filed: Jan. 23, 1989

[30] Foreign Application Priority Data

Feb. 2, 1988 [GB] United Kingdom ............... 8802219

[51] Int. Cl.$^5$ .............................................. C07F 9/02
[52] U.S. Cl. ...................................... 558/133; 556/19
[58] Field of Search ........................... 558/133; 556/19

[56] References Cited

U.S. PATENT DOCUMENTS 3,358,057 12/1967 Cherbuliez et al. ............... 558/133

OTHER PUBLICATIONS

Kosolapoff et al. "Organic Phosphorus Compounds", vol. 7, (1977), p. 86.
Derwent, Abstract of EP 245,207.
D. M. Puri, et al., J. Indian Chem. Soc. 49 77 (1972).
C. M. Mikulski et al., Inorg. Chim. Acta, 3,523(1969).

Primary Examiner—Mukund J. Shah
Assistant Examiner—C. Cseh
Attorney, Agent, or Firm—Luther A. R. Hall

[57] ABSTRACT

The present invention provides a process for producing a metal or metalloid salt of methyl methy phosphonic acid which comprises reacting, under non-aqueous conditions, dimethyl methylphosphonate with a finely divided form of an oxide or hydroxide of one or more metals or metalloids from group IIA, IIB, IIIA, IVA, IVB, VA, VIB, VIIB or VIII of the Periodic Chart of Elements, at an elevated temperature.

9 Claims, No Drawings

METHOD FOR PREPARATION OF METAL SALTS OF METHYL PHOSPHONIC ACIDS

The present invention relates to a method for the preparation of metal and metalloid salts of methyl methylphosphonic acid from dimethyl methylphosphonate (DMMP).

Metal salts of alkyl and functional alkyl phosphonic acid derivatives are disclosed as flame retardant additives for polyurethanes in EP No. 0 245 207. This specification describes several processes for producing the metal salts, but these processes suffer from various disadvantages when DMMP salts are produced. The by-products produced are hazardous e.g. methyl chloride, methyl ethers or acetate; are inorganic salts which cause environmental problems; or the process requires pure DMMP as starting material.

We have surprisingly found that salts from DMMP can be produced in good yield, without the formation of hazardous by-products, by reacting DMMP with a finely divided form of the metal oxide or hydroxide. By-products such as methanol are formed which can easily be removed and any unreacted DMMP can be easily recovered and re-used. The reaction is surprising because aluminium trihydrate for instance is used extensively as an inorganic flame retardant filler and is generally regarded as chemically inert.

Accordingly the present invention provides a process for producing metal or metalloid salts of methyl methylphosphonic acid which comprises reacting, under non-aqueous conditions, dimethyl methylphosphonate with a finely devided form of an oxide or hydroxide of one or more metals or metalloids from group IIA, IIB, IIIA, IVA, IVB, VA, VIB, VIIB and VIII of the Periodic Chart of Elements (Fisher Scientific Company C 1968), at an elevated temperature.

Thus the metal or metalloid may be selected from, for example, magnesium, calcium, barium, zinc, boron, aluminium, molybdenum, manganese, silicon, tin, lead, titanium, antimony, iron and cobalt. Preferably the metal is magnesium or aluminium.

Suitable metal or metalloid oxides and hydroxides include aluminium hydroxide, aluminium oxide, aluminium oxide mono- or tri-hydrate, antimony trioxide, antimony tetroxide, antimony pentoxide, barium hydroxide hexahydrate, barium oxide, barium peroxide hexahydrate, boric oxide, boric acid, calcium hydroxide, calcium oxide, calcium peroxide hexahydrate, cobalt hydroxide, cobalt(II) oxide, cobalt(III) oxide hexahydrate, iron(II) hydroxide, iron(II) oxide, iron(III) oxide, iron(III) oxide trihydrate, lead hydroxide, lead oxide, lead suboxide, lead sesquioxide, magnesium hydroxide, magnesium oxide, magnesium peroxide, manganese hydroxide, manganese oxide, manganese dioxide, manganese trioxide, molybdenum oxide, molybdenum hydroxide, silicon oxide, silicon dioxide, hydrated silicone dioxide, tin(II) oxide, tin(II) oxide monohydrate, tin(IV) oxide, tin(IV) oxide dihydrate, titanium oxide, titanium dioxide, titanium sesquioxide, zinc hydroxide, zinc oxide and zinc peroxide.

The finely divided form may have particles of an average size below 2 microns, preferably below 1 micron.

The reaction may be carried out at a temperature of from 100° to 200° C., preferably from 160° to 180° C. The reaction may use excess DMMP as reaction solvent or a suitable high boiling inert solvent may be used, for example xylene, chlorobenzene etc. and distilling off the methanol formed. Most preferably the reaction is carried out under reflux using DMMP as reaction solvent.

The process of the invention is free from any problems associated with inorganic by-products and their subsequent disposal. Unreacted DMMP may be recovered and reused and the methanol formed may be easily removed.

The products obtained by the process of the invention are suitable as flame retardant additives for polymers in the manner described in EP No. 0 245 207.

The phosphonic acid salts may be used in various polymers. Examples of polymers which may be rendered flame retardant are:

1. Polyphenylene oxides and sulfides, and blends of these polymers with polystyrene graft and copolymers such as high impact polystyrene, EPDM copolymers with rubbers.

2. Polyurethanes which are devided from polyethers, polyesters or polybutadiene with terminal hydroxyl groups on the one side and aliphatic or aromatic polyisocyanates on the other side including polyisocyanurates, as well as precursors thereof.

3. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance, with polyethylene glycol, polypropylene glycol or polytetramethylene glycols.

4. Polyesters which are derived from dicarboxylic acids and dialcohols and/or from hydroxycarboxylic acids or the corresponding lactones, such as polyethylene terephthalate, polybutylene terephthalate, poly-1,4-dimethylol-cyclohexane terephthalate and polyhydroxybenzoates as well as block-copolyether-esters derived from polyethers having hydroxyl end groups.

5. Unsaturated polyester resins which are derived from copolyesters of saturated and unsaturated dicarboxylic acids with polyhydric alcohols and vinyl compounds as crosslinking agents, and also halogen containing modifications thereof of low inflammability.

6. Polystyrene.

7. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with random copolymers of styrene or α-methylstyrene with dienes or acrylic derivatives, for instance the copolymer mixtures known as ABS-, MBS-, ASA- or AES-copolymers, and ABS/polycarbonates blends.

8. Cross-linked epoxide resins which are derived from polyepoxides, for example, from bis-glycidyl ethers of bisphenol A, or from cycloaliphatic diepoxides.

The invention is illustrated by the following Examples:

EXAMPLE 1

Monomethyl methylphosphonic acid aluminum salt 39.0 parts (0.5 mole) aluminium trihydroxide is added to 1000 milliliters of dimethyl methylphosphonate with very efficient mixing and the mixture is heated to reflux temperatures (180° C.±2° C.).

A thick slurry is formed after heating for 2 hours and sufficient dimethyl methylphosphonate is added to maintain efficient mixing subsequent distillation of the methanol formed.

The reaction mixture is heated for a further 6 hours at reflux temperatures and cooled. The solid product is collected, washed with 4×250 ml portions of water followed by 2×500 ml portions of acetone and dried at about 150° C. under reduced pressure to constant weight to give 168.0 parts of monomethyl methylphosphonic acid aluminium salt having melting point >250° C. and micro analysis % Al, 8.11; % P, 26.53; Calculated for $C_6H_{18}O_9P_3Al$: % Al, 7.63; % P, 26.27.

EXAMPLE 2

Using the procedure described in Example 1, 29.0 parts (0.5 mole) of finely divided magnesium hydroxide and 500 milliliters of dimethyl methylphosphonate are heated at reflux for 4 hours. The solid product is collected, washed with acetone and dried at 100° C. under vacuum to constant weight. There are obtained 62.6 parts of monomethyl methylphosphonic acid magnesium salt melting >230° C. and having micro analysis % Mg, 9.36; % P, 23.70; Calculated for $C_4H_{12}O_6P_2Mg \cdot H_2O$: % Mg, 9.23; % P, 23.85.

EXAMPLE 3

Using the procedure described in Example 1, 15.6 parts (0.2 mole) of aluminium trihydroxide 11.7 parts (0.2 mole) of magnesium hydroxide and 500 milliliters of dimethyl methylphosphonate give 61.0 parts of a mixed metal salt having melting point >200° C. and micro analysis % Al, 7.53, % Mg, 0.64, % P, 24.52.

EXAMPLE 4

Using the procedure described in Example 1, 25.5 parts (0.25 mole) of aluminia (Neutral Grade) and 124 parts (1.0 mole) of dimethyl methylphosphonate are heated at reflux for 6 hours. The solid product is collected, washed with water and dried to constant weight to give 37.8 parts of product having melting point >230° C. and micro analysis % Al, 15.35, % P, 9.79.

We claim:

1. A process for producing a metal or metalloid salt of methyl methylphosphonic acid which comprises reacting, under non-aqueous conditions, dimethyl methylphosphonate with a finely divided form having particles of an average size below 2 microns, of an oxide or hydroxide of one or more metals or metalloids from group IIA, IIB, IIIA, IVA, IVB, VA, VIB, VIIB or VIII of the Periodic Chart of Elements, at an elevated temperature.

2. A process as claimed in claim 1 in which the reaction temperature is from 100° C. to 200° C.

3. A process as claimed in claim 2 in which the reaction temeprature is from 160° to 180° C.

4. A process as claimed in claim 1 in which the reaction is carried out using excess dimethyl methylphosphonate as solvent, or a high boiling inert solvent.

5. A process as claimed in claim 1 in which the metal or metalloid is magnesium, calcium, barium, zinc, boron, manganese, molybdenum, aluminium, silicon, tin, lead, titanium, antimony, iron or cobalt.

6. A process as claimed in claim 5 in which the metal or metalloid is magnesium or aluminium.

7. A process as claimed in claim 1 in which the oxide or hydroxide has an average particle size below 1 micron.

8. A process as claimed in claim 5 in which the oxide or hydroxide has an average particle size below 1 micron.

9. A process as claimed in claim 8 in which the metal or metalloid is magnesium or aluminum.

* * * * *